United States Patent [19]

Bhattacharjee et al.

[11] Patent Number: 4,737,463

[45] Date of Patent: Apr. 12, 1988

[54] PHOTOACTIVATABLE TIME-TEMPERATURE INDICATOR

[75] Inventors: Himangshu R. Bhattacharjee, Randolph; James T. Yardley, Morristown; Thaddeus Prusik, Roosevelt; Ronald R. Chance, Morris Plains, all of N.J.

[73] Assignee: LifeLines Technology, Inc., Morris Plains, N.J.

[21] Appl. No.: 786,407

[22] Filed: Oct. 9, 1985

[51] Int. Cl.$^4$ .................... G01N 33/02; G01D 21/00
[52] U.S. Cl. .......................... 436/2; 436/7; 436/164; 436/905; 422/56; 422/58; 116/206; 116/216; 252/408.1
[58] Field of Search ............... 436/2, 7, 164, 58, 147, 436/905; 422/56, 57, 58; 252/408.1; 116/206, 207, 216; 526/285

[56] References Cited

U.S. PATENT DOCUMENTS

| | | | |
|---|---|---|---|
| 4,189,399 | 2/1980 | Patel | 252/408.1 |
| 4,208,186 | 6/1980 | Patel | 422/58 X |
| 4,212,153 | 7/1980 | Kydonieus | 116/216 X |
| 4,228,126 | 10/1980 | Patel et al. | 436/2 X |
| 4,238,352 | 12/1980 | Patel | 252/408.1 X |
| 4,276,190 | 6/1981 | Patel | 252/408.1 |
| 4,298,348 | 11/1981 | Ivory | 436/7 |
| 4,373,032 | 2/1983 | Preziosi | 526/285 X |
| 4,439,517 | 3/1984 | Irving | 430/328 |
| 4,511,641 | 4/1985 | Busman et al. | 430/158 |
| 4,533,640 | 8/1985 | Shafer | 422/58 X |

OTHER PUBLICATIONS

J. V. Crivello, Polymer Eng. and Sci., 23, (1983), pp. 953-956.
J. V. Crivello, J. Polymer Sci., Symposium, 56, (1976), pp. 383-395.
S. Moslowski, Appl. Optics, 13, (1974), pp. 857-860.

Primary Examiner—Barry S. Richman
Assistant Examiner—J. Johnston
Attorney, Agent, or Firm—Arthur J. Plantamura

[57] ABSTRACT

A photoactivated time-temperature indicator is based on diacetylenic salts. A thermally unreactive ("inactive") diacetylenic salt (or a mixture of such salts) is mixed, in a polymeric matrix, with a material that generates acid upon exposure to light. Photoexcitation, preferably by UV or near UV light, causes the formation of a thermal reactive ("active") free diacetylenic acid. Following this activation step, a progressive color development occurs at a rate that increases with temperature. The indicator is useful for monitoring the freshness of perishable products, particularly those that require refrigeration.

23 Claims, 4 Drawing Sheets

PHOTOACTIVATABLE TIME-TEMPERATURE INDICATOR

DESCRIPTION

BACKGROUND OF THE INVENTION

1. Field of the Invention

This invention relates to an environmental exposure indicator and, more particularly, to an indicator that is inactive until it is activated by actinic radiation.

2. Description of the Prior Art

Several patents have disclosed the use of color-changing indicators to monitor the time-temperature history of perishables. Among these are U.S. Pat. No. 4,189,399, issued Feb. 19, 1980, to Patel; and U.S. Pat. No. 4,212,153, issued July 15, 1980, go Kydonieus et al.

When the perishable to be monitored has a short useful lifetime and/or requires refrigeration, then it is desirable, if not essential, to use an indicator that is inactive until activated. Patel, U.S. Pat. Nos. 4,208,187, issued June 17, 1980, and 4,276,190, issued June 30, 1981, disclosed diacetylenic compositions having an inactive form that is activated by contact with an activating vapor. Activation of a diacetylenic monomer in salt form by conversion to the acid form was disclosed in U.S. Pat. No. 4,373,032, issued Feb. 9, 1983, to Preziosi et al.

Photoactivation of a variety of chemical processes has been reported. It is known, for example, that certain onium salts are photoinitiators of cationic polymerization (see, e.g., J. V. Crivello, Polymer Eng. and Sci. 3, 953 (1983); and J. V. Crivello et al., J. Polymer Sci., Symposium No. 56, 383 (1976)).

Photogeneration of a hydrohalic acid has been disclosed by S. Maslowski, Appl. Optics 13, 857 (1974) and in U.S. Pat. No. 4,247,611, issued Jan. 27, 1981, to Sander et al.

SUMMARY OF THE INVENTION

In accordance with the present invention, a photoactivatable time-temperature indicator comprises a mixture of:

(a) a thermally unreactive diacetylenic compound and (b) a photosensitive compound that, on exposure to actinic radiation, forms an acid that converts the diacetylene to a thermally reactive product. Preferably, the mixture is in a medium that facilitates transport between the diacetylenic compound and the photogenerated acid.

In operation, the present invention provides a process for measuring incremental environmental exposure, which comprises the steps:

(a) exposing a photoactivatable indicator to actinic radiation to render it thermally reactive, (b) measuring the reflectivity of the indicator at a specified wavelength, (c) measuring the reflectivity of the indicator at the specified wavelength after environmental exposure, and (d) calculating the incremental environmental exposure by using a pre-established relationship between a change in reflectivity of the indicator and environmental exposure. The process is particularly useful for measuring the incremental environmental exposure of a perishable article, which involves first applying to the article a photoactivatable time-temperature indicator and then following the steps set forth above.

The term "time-temperature indicator," as it is used in the present specification and claims, refers to a composition that responds in a measurable and predictable way to the integrated effect of time and temperature. The activation of the time-temperature indicators of this invention is by photogeneration of an "acid," which term is understood to include Lewis acids, Bronsted acids, and the like.

DETAILED DESCRIPTION OF THE INVENTION

Figure 1:
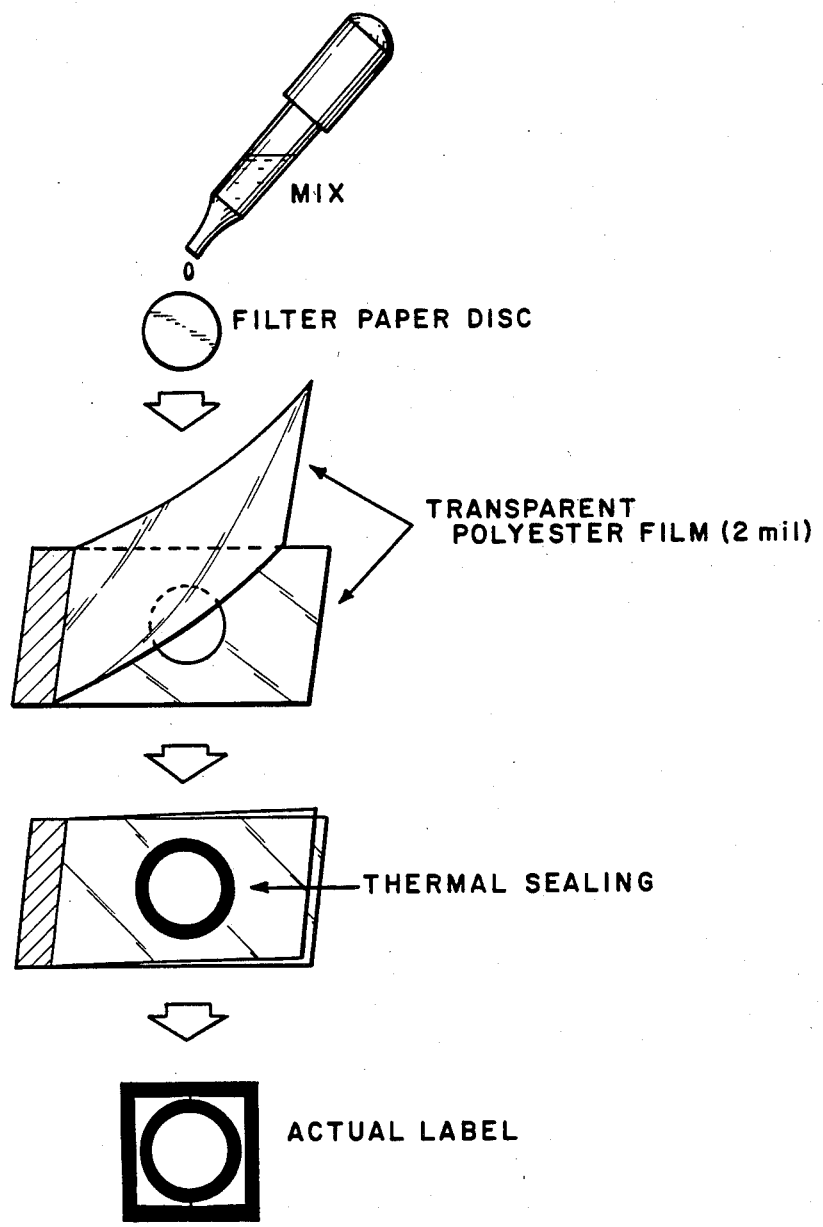
FIG. 1 is a schematic that illustrates the preparation of a sealed indicator label of the present invention.

Many articles of commerce—both food and non-food—are perishable. Particularly when the perishable is enclosed in packaging, it may not be readily apparent when the article has exceeded its useful lifetime. It is even more difficult to determine precisely where an article is positioned on an imaginary graph that plots its deterioration as a function of time. Since the rate at which a perishable deteriorates is generally a function of its integrated time-temperature exposure—at least within a restricted range of time-temperature—a time-temperature indicator is a useful tool for those who are concerned with the freshness of perishable products. The indicator must comprise a composition that provides a readily-measurable physical property that changes in a reproducible way with exposure to time-temperature. For convenience, we use color, but other properties are also suitable. For a real-time indicator, the time frame over which the color changes, in the temperature range of interest, must correspond to that over which the perishable product deteriorates.

For products that undergo significant changes over relatively short times (a few days, for example) or at relatively low temperatures (zero degrees Celsius, for example) some form of controlled activation is required to assure that color change does not begin until the desired point in time. One possible means of activation is with light or "photoactivation." Potential advantages of photoactivation include (i) activation of color change at a specified point in time, (ii) totally non-intrusive nature of activation process, and (iii) possibility of controlling extent of activation by photodose, thereby providing a range of time-temperature characteristics with a single indicator.

Some disadvantages or concerns include (i) possibility of activation by ambient light exposure, (ii) potential difficulties in reproducing activation dose, and (iii) possible acceleration of color change due to activating radiation.

Certain diacetylenic salts, designated for convenience as MOOC-DA, are inactive either in crystalline form or in solution, while the corresponding free acid HOOC-DA is active in crystalline form. In aqueous media, salts of acids generally precipitate out as crystalline materials as the pH of the system is lowered below the $pK_a$ of the acid:

$$H^+ + {}^-OOC\text{-}DA \rightleftharpoons HOOC\text{-}DA \text{ (xtal)} \qquad (a)$$

Preferred diacetylenic compounds for the present invention are of the form
(A) a salt of $[HOOC-(CH_2)_n-C\equiv C-C\equiv C-(CH_2)_2-C\equiv C]_2$
(B) a salt of $[HOOC-(CH_2)_n-C\equiv C-C\equiv C-CH_2]_2$
and mixtures thereof, where n is in the range 1–7.

A number of chemical compounds are known to generate acids upon excitation with actinic radiation. In aqueous media the acid so produced can lower the system pH, so long as the $pK_a$ of the acid is less than the pH of the medium (at least to a first approximation). Thus, if an aqueous medium containing a diacetylenic salt (at pH above the $pK_a$ for the diacetylenic acid) is combined with a material that photogenerates strong acid, then excitation by actinic radiation can lower the pH of the medium. In this way, an active form of diacetylene can be precipitated.

A number of considerations should be taken into account in optimizing such a system:

Photoactivation of the acid should occur at wavelengths long enough that photopolymerization of the diacetylene does not occur. Typically, this means that wavelengths longer than 300 nm should be used. A UV screen cover sheet, which passes radiation only at wavelengths longer than 350 nm, is a convenient means to prevent photopolymerization by ambient radiation, while still passing the actinic radiation needed for photoactivation. Thus, activating wavelengths longer than 350 nm are preferred and polyester is a preferred cover sheet material.

But long activating wavelengths can also cause problems. If time-temperature exposure is monitored by changes in reflection density, then it is important that the light whose reflection is being measured not be capable of causing additional activation. Since it is convenient to use visible-light reflection, preferably there should be no activation at wavelengths longer than 400 nm. Thus, a material absorbing at wavelengths shorter than 400 nm and activatable at wavelengths longer than 300 nm, preferably longer than 350 nm, would be desired for the photoacid. In some cases, an opaque covering may be necessary to prevent unintended activation by ambient radiation.

A photoreaction that could easily be driven to completion might be desirable, since the resultant activation could be relatively independent of precise radiation dose. On the other hand, if different levels of photoactivation are generated by different doses of actinic radiation, then a single material can serve as an indicator over a wide range of time and temperature.

The photoacid should be thermally stable in the application environment; i.e., it should not be thermally activatable.

Transport phenomena must be taken into account. For example, in a highly viscous medium, the crystallization process might be too slow for the desired time-temperature indication. Also, transport of $H^+$ ions must be sufficient to allow reaction (a) to occur on the appropriate timescale.

Although the aqueous medium must permit sufficient mass transport to provide the necessary change in pH, preferably it can be coated onto paper, plastic, or other suitable absorbent substrate. Filter paper is a preferred substrate.

The need for a UV screen to shield the indicator from polymerization and the need to permit mass transport can be addressed simultaneously by sealing the indicator between a cover sheet and a base sheet to form a label. A sealed label would provide several advantages:

(1) The label can be made rather inexpensively.

(2) The sealed system can provide the advantage of easy handling.

(3) Wide varieties of clear plastic materials are available that can easily be sealed off thermally, can provide an oxygen and moisture barrier, and can block light having wavelength less than 300 nm to prevent photopolymerization of the diacetylene.

(4) Once laminated, the label can be stored in the dark for an extended period and the system can be put in operation when required by exposing the label to actinic radiation.

Preferred diacetylenic compounds for the present invention are the salts, preferably the sodium salts, of the acids $$[HOOC-(CH_2)_3-C\equiv C-C\equiv C-(CH_2)_2-C\equiv C]_2 \qquad (I)$$
"Hexayne Free Acid"

$$[HOOC-(CH_2)_3-C\equiv C-C\equiv C-CH]_2 \qquad (II)$$
"Tetrayne Free Acid"

and mixtures thereof. The salts are inactive as t-T indicators, while the corresponding free acids are active.

o-Nitrobenzaldehyde efficiently undergoes photochemical conversion to the corresponding nitrosobenzoic acid:

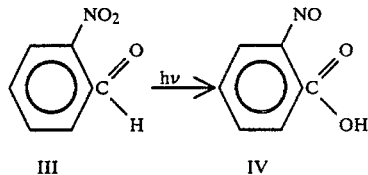

III        IV

Compared with normal aliphatic carboxylic acids ($pK_a \sim 4.8$), benzoic acids are strong acids ($pK_a \sim 4.2$) and benzoic acids that are orthosubstituted with electron withdrawing groups are stronger yet (o-nitrobenzoic acid, $pK_a \sim 2.2$; o-chlorobenzoic acid, $pK_a \sim 2.9$). Thus, o-nitrosobenzoic acid (IV) is a strong acid relative to aliphatic carboxylic acids.

An alternative to o-nitrobenzaldehyde for the photosensitive compound is 2,2,2-tribromoethanol ($CBr_3CH_2OH$). This compound generates HBr when it is exposed to UV light. A drawback of the compound is that activation requires a light of wavelength about 260 nm or less, which can cause undesirable polymerization of the diacetylene. Compared with a system using o-nitrobenzaldehyde, a 2,2,2-tribromoethanol system also responds more slowly at a given temperature.

Preferably, the medium that surrounds the diacetylenic and photosensitive compounds comprises a polymer, such as polyvinyl alcohol (PVA) or gelatin. A preferred medium is PVA that is 50–100 percent hydrolyzed or, more preferably 70–90 percent hydrolyzed. The weight-averaged molecular weight of the PVA may be in the range from about 500 to about 500,000, with about 110,000 preferred.

The following examples are presented in order to provide a more complete understanding of the invention. The specific techniques, conditions, materials, and reported data set forth to illustrate the principles and practices of the invention are exemplary and should not be construed as limiting the scope of the invention.

EXAMPLE 1

An aqueous medium was prepared by partial hydrolysis of a PVA obtained from Aldrich, which had a molecular weight of 115,000. An ultraviolet-transparent medium was prepared by mixing 2 grams of polymer in 100 mL of water. Into 5 mL of the medium was placed 0.015 g of a mixture of compounds I and II (denoted I-II) and 0.012 g of finely ground o-nitrobenzaldehyde (III). Four identical 2 mm cuvettes were filled with the resulting viscous solution. Cuvettes C and D were irradiated for 10 seconds with a commercial UV lamp (100 W Mercury Lamp, Oriel Corp.). Cuvettes B and D were placed in an oven at 60° C., while cuvettes A and C were maintained at room temperature. After 24 hours the cuvettes were examined visually. The contents of cuvettes A, B, and C were colorless, while those of cuvette D had turned dark purple as indicated in the table:

| Sample | Irradiation | Time  | Temperature | Color       |
|--------|-------------|-------|-------------|-------------|
| A      | No          | 24 hr | 20° C.      | none        |
| B      | No          | 24 hr | 60° C.      | none        |
| C      | Yes         | 24 hr | 20° C.      | none        |
| D      | Yes         | 24 hr | 60° C.      | dark purple |

Unactivated samples remain colorless for several days at 60° C.

EXAMPLE 2

Three strips of white filter paper (Whatman No. 41, 5 cm × 1.5 cm) were saturated with the solution described in Example 1. Strips A and B were irradiated with light from the same lamp for 20 sec, after which both strips became slightly blue. Strip A was heated with a hot air gun for few seconds. This strip turned red while strip B remained slightly blue. Strip C (not activated) exhibited no color change when heated in a similar manner.

EXAMPLE 3

Strips prepared as above were laminated between pieces of polyethylene film. Strips A and B were irradiated for 90 sec as described above. Strips B and C were placed in an oven at 60° C. for 120 minutes. Strip B turned red while strip C remained colorless and strip A remained slightly blue. These observations are summarized in the following table.

| Sample | Irradiation | Time     | Temperature | Color      |
|--------|-------------|----------|-------------|------------|
| A      | Yes         | 120 min. | 20° C.      | light blue |
| B      | Yes         | 120 min. | 60° C.      | red        |
| C      | No          | 120 min. | 60° C.      | colorless  |

EXAMPLE 4

Indicator labels were prepared as follows:

A polymeric gel was prepared by dissolving 4 g of 99-100% hydrolyzed, 115,000 MW PVA powder (purchased from Aldrich, Cat. #18251-6) in 100 mL water at 80° C. The coating mixture ("mix") was prepared by grinding together equal amounts (8 mg each) of compounds III and I-II in 1 mL of the gel.

A disc of filter paper (1 cm diameter) as then soaked thoroughly in the "mix" and the resulting coated piece was placed between two sheets of transparent, heat-sealable polyester film (obtained from Kapak Corp.). The excess fluid was removed by rubbing the top surface of the film with a paper towel. The edge of the film surrounding the piece of filter paper was then thermally sealed. The excess film areas were trimmed off and the labels were washed in water and stored in the dark at room temperature. The steps involved in the lamination procedure are shown in FIG. 1.

Photoactivation of the labels was accomplished by irradiating each with an Oriel 100 W mercury arc lamp for 60 sec under identical conditions. Polyester film filtered out light having a wavelength shorter than 300 nm.

Once activated, the extent of t-T color response due to thermal polymerization of the active free acid was monitored spectrophotometrically as follows. A Perkin-Elmer UV-visible spectrophotometer Model 553, with an integrating sphere attachment, was used to record spectra in the visible region. The integrating sphere attachment was calibrated to 100% reading for a wavelength of 400-750 nm in reflectance measurements by mounting unactivated labels in the reference and the sample holders. The holders were designed to accept samples of 1.2 cm × 2.2 cm minimum. Therefore, black masks with 1 cm circular opening were used to accommodate the samples. This modification was necessary to obtain a reasonable signal-to-noise ratio and to obtain good reproducibility. During the measurements of the progressive color change, the activated label replaced the unactivated one in the sample holder. The color change due to partial polymerization was measured either directly as a decrease in reflectivity (%R) or as $-\log R$, which is roughly equivalent to absorbance.

Figure 2:
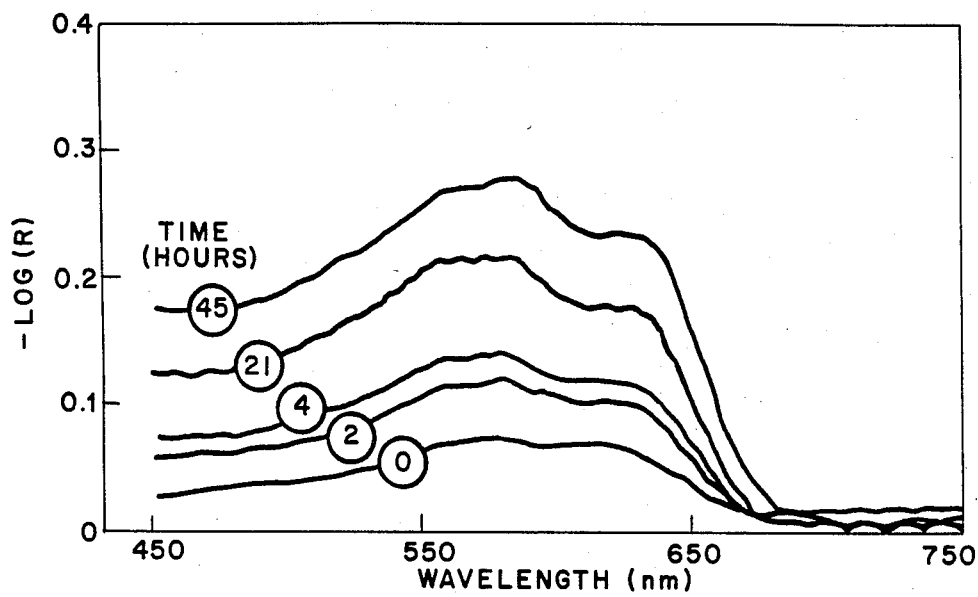
FIG. 2 depicts the time dependence of reflectivity spectra of an activated system of the present invention held at room temperature.
Figure 3:
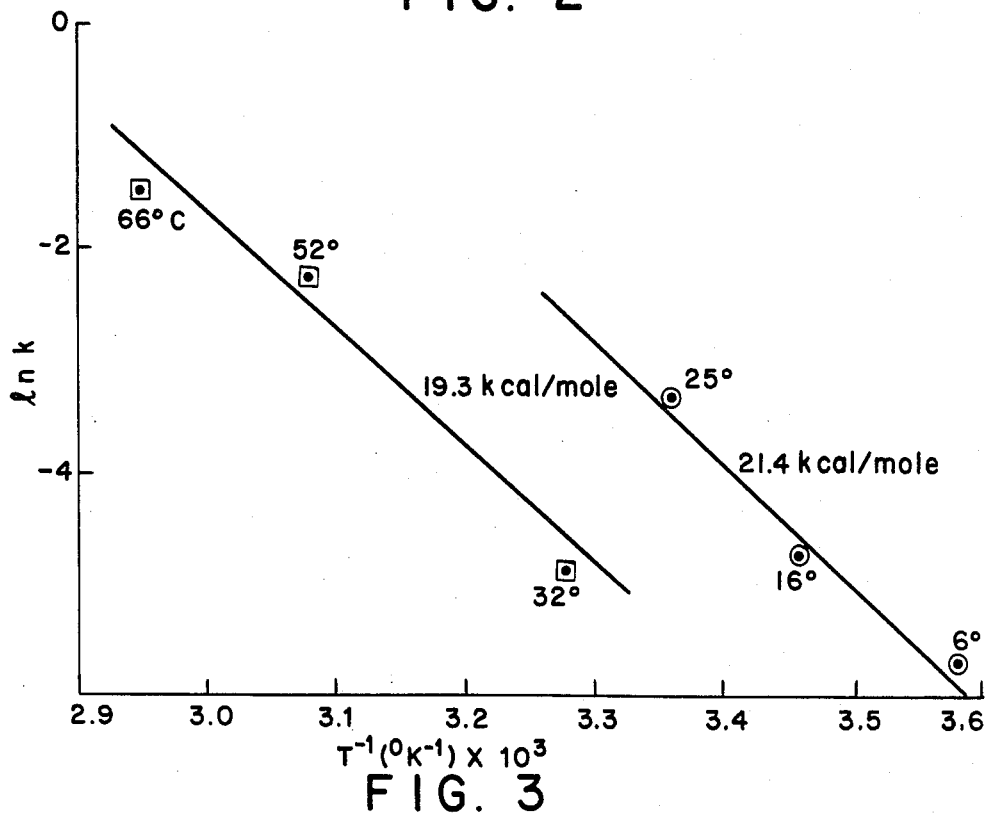
FIG. 3 depicts plots of data that yield the activation energy of the system of FIG. 2.
Figure 4:
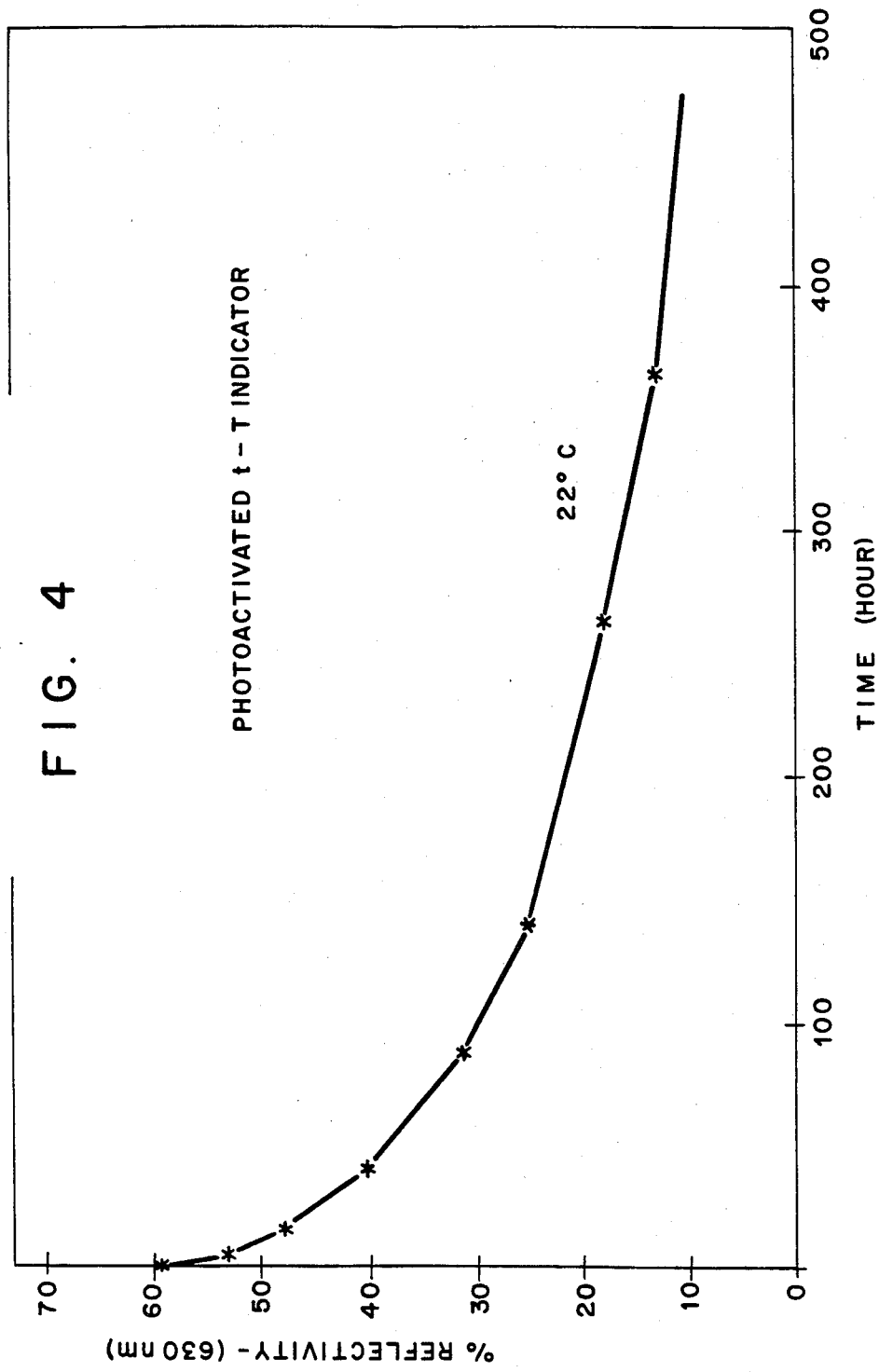
FIG. 4 depicts the time dependence of reflectivity at 630 nm of an activated indicator label of the present invention held at room temperature.

FIG. 2 shows representative spectra as a function of time for the samples held at 21° C. With time, progressive bands appeared at 580 nm and 630 nm. Absorbances at 630 nm were plotted as a function of time to obtain a measure of the relative reaction rate. The rate data were tested for samples held at two different ranges of temperatures. In one set of experiments, the samples were held at 66° C., 52° C. and 32° C.; in another set, the temperatures were 25° C., 16° C. and 6° C. (refrigeration temperature). The initial slopes of the rate plots gave relative rate constant, k, in units of absorbance hr$^{-1}$. In FIG. 3 the values of k obtained from the two sets were plotted as ln k vs. T$^{-1}$ to obtain the activation energy. Both sets of measurements gave an activation energy of approximately 20 kcals/mole. These results suggest that mass-transport phenomena are not the limiting factor in this system, down to temperatures as low as 6° C.

The decrease in reflectance was also monitored using an optical scanning wand that reads black and white reference bar codes and quantitatively measures the reflectance of a colored element relative to the reference bars. The scanner system employs 632 nm light output. Measurements with the optical wand showed sample reflectivities decreased from approximately 70% (after 80 sec. of photoactivation) to a minimum of approximately 15% with time-temperature evolution. This decrease occurred in 10 days at room temperature. A typical plot of reflectivity vs. time is shown in FIG.

Figure 5:
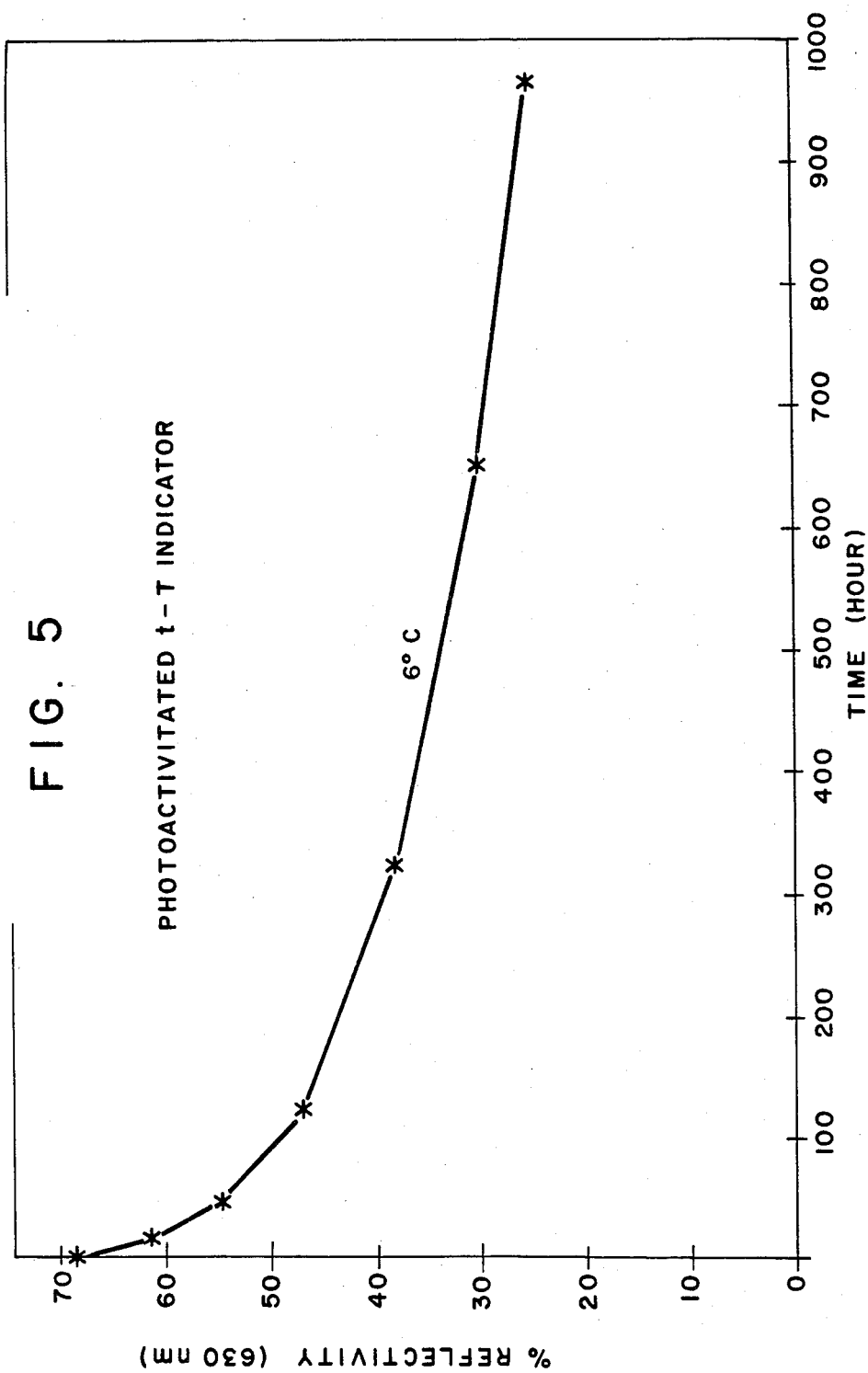
FIG. 5 depicts the time dependence of reflectivity at 630 nm of the label of FIG. 4 held at 6° C.

4. All reflectivity values are averages of at least ten scans. Typical results showing color change of an activated indicator with time at 6° C. appear in FIG. 5. As expected, color change at 6° C. was found to be rather slow. However, progressive color chnage was observed, and final color developed over a period of a few weeks. The measurements with the wand correlated well with those obtained from the Perkin-Elmer instrument.

Photoactivation always produced a faint blue color and the final color developed as deep blue-violet. Once activated, the progressive color development appeared almost the same for samples left either in the dark or under room light (monitored by measuring %R at 630 nm) provided temperature remained constant.

Results with different periods of photoactivation in the range from 30–120 sec show that the thermal activation rate for these indicators depends upon the amount of photoacid production.

We claim:

1. A photoactivatable time-temperature indicator, comprising a mixture of
   (a) a thermally unreactive diacetylenic compound,
   (b) a photosensitive compound that, on exposure to actinic radiation, forms an acid that converts the diacetylene to a thermally reactive product, and
   (c) an aqueous polymeric medium;
   said mixture forming a solution wherein transport between the diacetylenic compound and photogenerated acid is facilitated;
   said photoactivatable time-temperature indicator capable of being photoactivated with differing doses of actinic radiation whereby the period of time of the progressive color-developing temperature response to said indicator may be established at preselected ranges.

2. The indicator of claim 1 in which the photosensitive compound is o-nitrobenzaldehyde.

3. The indicator of claim 1 in which the photosensitive compound is 2,2,2-tribromoethanol.

4. The indicator of claim 1 in which the polymeric medium comprises gelatin.

5. The indicator of claim 1 further comprising an absorbent substrate in which the mixture is absorbed.

6. The indicator of claim 5 in which the absorbent substrate comprises filter paper.

7. The indicator of claim 1 further comprising a cover sheet over the mixture that is substantially transparent to the actinic radiation.

8. The indicator of claim 7 in which the cover sheet is a polyester.

9. The indicator of claim 1 in which the diacetylenic compound is selected from the group consisting of
   (A) a salt of $[HOOC-(CH_2)_n-C\equiv C-C\equiv C-(CH_2)_2-C\equiv C]_2$
   (B) a salt of $[HOOC-(CH_2)_n-C\equiv C-C\equiv C-CH_2]_2$
   and mixtures thereof, where n is in the range 1–7.

10. The indicator of claim 9 in which n=3.

11. The indicator of claim 10 in which the salt comprises a sodium salt.

12. The indicator of claim 1 in which the polymeric medium comprises polyvinyl alcohol.

13. The indicator of claim 12 in which the polyvinyl alcohol is 50–100% hydrolyzed.

14. The indicator of claim 13 in which the polyvinyl alcohol is 70–90% hydrolyzed.

15. The indicator of claim 12 in which the polyvinyl alcohol has a weight-averaged molecular weight in the range from about 500 to 500,000.

16. The indicator of claim 15 in which the polyvinyl alcohol has a weight-averaged molecular weight of about 110,000.

17. A method of measuring time-temperature exposure, which comprises the steps:
    (a) exposing a photoactivatable time-temperature indicator to actinic radiation to render it thermally reactive,
    (b) measuring the reflectivity of the indicator at a specified wavelength prior to the time-temperature exposure,
    (c) measuring the reflectivity of the indicator at the specified wavelength after the time-temperature exposure, and
    (d) calculating the incremental time-temperature exposure by using a pre-established relationship between a change in reflectivity of the indicator and time-temperature exposure.

18. The method of claim 17 in which the time-temperature exposure comprises a temperature in the range between about 6° and 60° C.

19. A method of mesuring the time-temperature exposure of a perishable article by applying to the article a photoactivatable time-temperature indicator and then following the steps of claim 17.

20. The method of claim 17 in which the photoactivatable time-temperature indicator comprises a mixture of a thermally unreactive diacetylenic compound and a photosensitive compound that, on exposure to actinic radiation, forms an acid that converts the diacetylenic compound to a thermally reactive product.

21. The method of claim 20 in which the photoactivatable time-temperatue indicator is a mixture of o-nitrobenzaldehyde,
    (A) a salt of $[HOOC-(CH_2)_3-C\equiv C-C\equiv C-(CH_2)_2-C\equiv C]_2$,
    (B) a salt of $[HOOC-(CH_2)_3-C\equiv C-C\equiv C-CH_2]_2$,
    and polyvinyl alcohol.

22. The method of claim 21 in which the actinic radiation is electromagnetic radiation having a wavelength in the range between about 250 nm and about 400 nm.

23. A sealed photoactivatable time-temperature label that comprises:
    (a) a mixture of
        (i) a thermally unreactive diacetylenic compound and
        (ii) a photosensitive compound that, on exposure to actinic radiation, forms an acid that converts the diacetylenic compound to a thermally reactive product,
    (b) an aqueous polymeric medium that contains the mixture and that facilitates transport between the diacetylenic compound and the photogenerated acid,
    (c) a polyester cover sheet over the mixture, and
    (d) a base sheet that seals against the cover sheet, sandwiching the polymeric medium and mixture between the sheets wherein said photoactivatable time-temperature indicator-label is capable of being photoactivated with differing doses of actinic radiation whereby the period of time of the progressive color-developing temperature response of said label may be established at preselected ranges.

* * * * *